US00PP35543P2

(12) United States Plant Patent
Kamstra

(10) Patent No.: US PP35,543 P2
(45) Date of Patent: Dec. 12, 2023

(54) POINSETTIA PLANT NAMED 'EURZ0027'

(50) Latin Name: *Euphorbia pulcherrima*
Varietal Denomination: EURZ0027

(71) Applicant: SYNGENTA CROP PROTECTION AG, Basel (CH)

(72) Inventor: Silvan Adelmar Kamstra, Andijk (NL)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 18/094,561

(22) Filed: Jan. 9, 2023

(51) Int. Cl.
*A01H 5/02* (2018.01)
*A01H 6/38* (2018.01)

(52) U.S. Cl.
USPC ..... Plt./307
CPC ..... *A01H 6/385* (2018.05)

(58) Field of Classification Search
USPC ..... Plt./307
CPC ..... A01H 5/02
See application file for complete search history.

(56) References Cited

PUBLICATIONS

CPVO Application Consultation Version 4.7.11 Citation for 'EURZ0027'; Apr. 21, 2023; 2 pages.*

* cited by examiner

*Primary Examiner* — Kent L Bell
(74) *Attorney, Agent, or Firm* — Dale Skalla

(57) ABSTRACT

A new *Poinsettia* plant named 'EURZ0027' particularly distinguished by the distinct dark red bract color, dark green foliage, and strong vigor with very good branching and strong stems.

1 Drawing Sheet

Latin name of the genus and species of the plant claimed: *Euphorbia pulcherrima.*

Varietal denomination: 'EURZ0027'.

BACKGROUND OF THE NEW PLANT

The present invention comprises a new *Poinsettia*, botanically known as *Euphorbia pulcherrima*, and hereinafter referred to by the variety name 'EURZ0027'.

'EURZ0027' is a product of a designed crossing between a female plant called '34704' and a male plant called '33910'. Both parents are unpatented breeding plants. '34704' has wavy leafs and small cyathia. '33910' has relative small bracts. The new cultivar has dark red bract color. The variety has large size inflorescences with bracts a little upright directed, dark green foliage, small cyathia and very strong vigor with good branching.

'EURZ0027' originates from a cross made in 2015 in Enkhuizen, The Netherlands.

A greenhouse crop was developed from the first selected plant by making cuttings and these plants were evaluated in Enkhuizen, The Netherlands. The plants were multiplied by cuttings separately and examined during next falls-winters flowering for uniformity and stability of the new combination of characteristics in Enkhuizen, The Netherlands.

BRIEF SUMMARY OF INVENTION

Horticultural examination of plants grown from cuttings of the plant initiated in April 2018, and continuing thereafter, has demonstrated that the combination of characteristics as herein disclosed for 'EURZ0027' are firmly fixed and are retained through successive generations of asexual reproduction.

'EURZ0027' has not been observed under all possible environmental conditions. The phenotype may vary significantly with variations in environment such as temperature, light intensity and day length.

A Plant Breeder's Right for this cultivar was applied for in the European Union on Feb. 10, 2023, No. 2023/0371. 'EURZ0027' has not been made publicly available prior to the effective filing date of this application, notwithstanding any disclosure that may have been made less than one year prior to the effective filing date of this application by the inventor or another who obtained 'EURZ0027' directly from the inventor.

The following traits have been repeatedly observed and are determined to be basic characteristics of the new variety. The combination of these characteristics distinguishes this *Poinsettia* as a new and distinct variety.

BRIEF DESCRIPTION OF THE PHOTOGRAPHS

The accompanying photographic drawings show typical flower and foliage characteristics of 'EURZ0027' with colors being as true as possible with an illustration of this type. The photographic drawings show flowering potted plants of the new variety.

Figure 1:
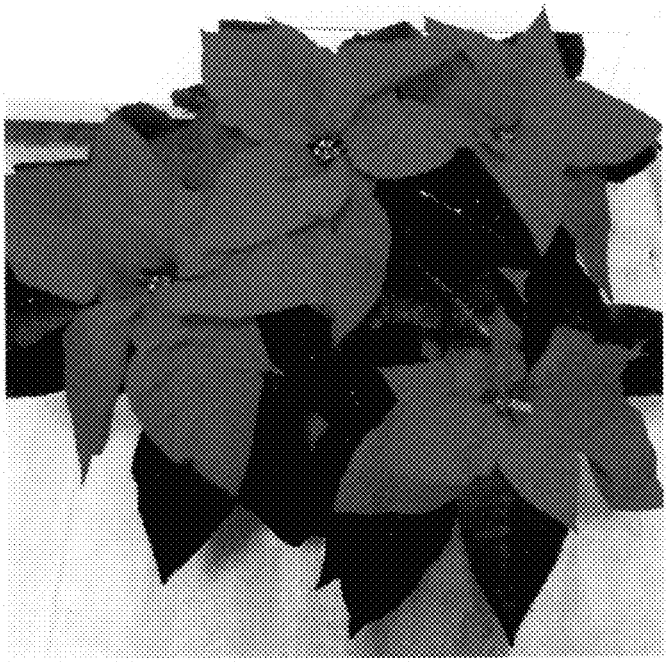

FIG. 1 was taken on Dec. 9, 2022 and shows a view of the bracts from the top of plant, on a plant about 22 weeks old.

Figure 2:
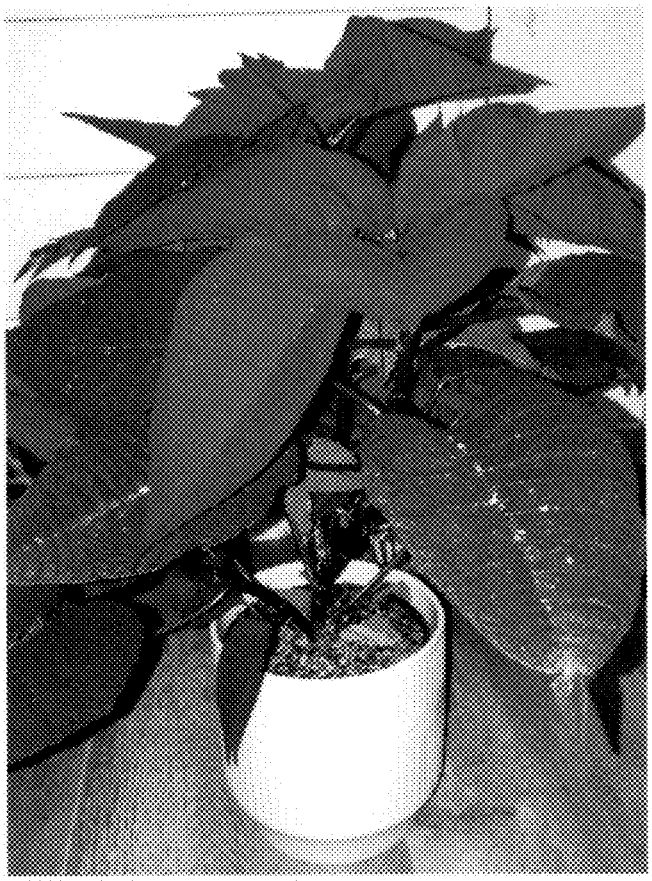

FIG. 2 was taken on Dec. 9, 2022 and shows a side view of the same plant.

DETAILED BOTANICAL DESCRIPTION

The measurements were taken in Enkhuizen, The Netherlands in December 2022 on 22 weeks old plants growing in a greenhouse. Culture of these plants had started in late June 2022 with planting rooted cuttings in 13 cm pots and terminal pinching about 2 weeks later. The plants were grown under natural day light in the fall (no black cloth to initiate earlier flowering) and at the moderately warm temperature of 18°-20° C. for the bench heating without any applications of PGR.

Color references are made to The Royal Horticultural Society Colour Chart (RHS) 2001.

TABLE 1

DIFFERENCES BETWEEN THE NEW VARIETY 'EURZ0027' AND A SIMILAR VARIETY 'EURZ0009'

| | 'EURZ0027' | 'EURZ0009', U.S. Plant Pat. No. 30,545 |
|---|---|---|
| Plant height: | 30 cm | 30 cm |
| Cyathia size: | 0.2 cm | 0.6 cm |
| Bract color: | 46A | 45B |

Plant:

*Form, growth and habit.*—Shrub, with the branches slanting upright, good branching.

*Plant height* (*inflorescence included*).—30 cm.

*Plant width.*—35-40 cm.

Roots:

*Number of days to initiate roots.*—18-20 days at about 24 degrees C.

*Number of days to produce a rooted cutting.*—24-26 days at 24 degrees C.

*Type.*—Fine, fibrous, free branching.

*Color.*—A mix of RHS N155C and 165C.

Foliage:

*Arrangement.*—Alternate, 8-11 leaves per branch.

*Immature, leaf color, upper surface.*—Approximately RHS 136A.

*Lower surface.*—RHS 139A.

*Mature, leaf color, upper surface.*—RHS 136A.

*Lower surface.*—RHS 139A.

*Length.*—11-12 cm.

*Width.*—7-8 cm.

*Shape.*—Ovate, with almost no lobes.

*Base shape.*—Obtuse to rounded.

*Apex shape.*—Acuminate.

*Venation pattern.*—Pinnate.

*Margin.*—Entire; lobes, when present acuminate.

*Aspect.*—Leaf blades are slightly downwards directed.

*Texture, upper surface.*—Smooth.

*Lower surface.*—Smooth, apart from the protruding veins.

*Color of veins, upper surface.*—In between RHS 139A and 139B.

*Color of veins, lower surface.*—Central vein RHS 184A.

*Petiole color, upper surface.*—RHS 185A.

*Lower surface.*—RHS 184A.

*Length.*—6-7 cm.

*Diameter.*—0.30 cm.

*Aspect.*—Slightly upward directed.

*Texture.*—Glabrous.

Stem:

*Quantity of main branches per plant.*—About 6 to 8.

*Color of stem.*—RHS 139A with RHS 183B.

*Length of stem.*—20-23 cm.

*Diameter.*—0.6-0.8 cm.

*Length of internodes.*—1-3.5 cm.

*Texture.*—Glabrous.

*Color of peduncle.*—RHS 139A with RHS 183B.

*Length of peduncle.*—0.2-0.3 cm.

*Peduncle diameter.*—0.2 cm.

*Texture.*—Glabrous.

Inflorescence:

*Type.*—Terminal cyme with surrounding whorl of colored bracts.

*Flowering, botanically* (*opening of the stamen, shedding of pollen*).—End November/early December.

*Flowering, commercially* (*sufficiently colored bracts*).—Mid November/end November.

*Flowering response time.*—About 8 weeks from equinox.

*Duration of flowering.*—Depends on light and environment, at least 4-6 weeks of shelf life.

*Fragrance.*—Absent.

*Shape of inflorescence.*—Rosette-like whorl, star-shaped; bracts borne nearly horizontally to weakly funnel-shaped (slanting upright); tight center.

*Diameter of inflorescence.*—25 cm.

*Inflorescence, vertical diameter.*—5-6 cm.

*Number of completely colored bracts per inflorescence* (*sized over 2 cm*).—9-11.

*Single bract, shape.*—Ovate with relatively long, pointed tips, without weak lobes.

*Bract, apex.*—Acuminate.

*Bract, base.*—Weakly rounded.

*Single bract, length of blade.*—Up to 12 cm, younger bracts diminishing in size.

*Single bract, width of blade.*—Up to 8 cm, younger bract diminishing in size.

*Bract margin.*—Entire; lobes, when present accuminate.

*Bract venation pattern.*—Pinnate.

*Bract color, upper side.*—RHS 46A.

*Bract color, lower side.*—RHS 46A.

*Vein color, upper surface.*—RHS 46A.

*Vein color, lower surface.*—Approximately RHS 46A.

*Texture, upper and lower surface.*—Weakly rugose, glabrous.

*Bract petiole color, upper surface.*—RHS 185A.

*Bract petiole color, lower surface.*—RHS 185A.

*Bract petiole, length.*—About 3 cm, shorter with younger bracts.

*Bract petiole diameter.*—0.2-0.3 cm.

Cyme (true inflorescence):

*Cyme, diameter.*—1.0-1.5 cm.

*Number of cyathia.*—5, borne in a tight cluster.

*Cyathium, shape.*—Ovate.

*Cyathium, diameter.*—0.2 cm.

*Cyathium, length.*—0.4 cm.

*Color.*—RHS 143B, top is RHS 145A.

*Nectar cups.*—Irregularly 1 per cyathium.

*Nectur cup, width.*—0.2 cm.

*Nectar cup, color.*—RHS 144B.

Reproductive organs:

*Stamen* (*actually reduced male florets*).—Usually in a small bunch of 5-10 at the top of the cyathium.

*Shape.*—Strap-like.

*Filament length.*—0.2 cm.

*Filament color.*—RHS 53B.

*Anther color.*—RHS 46A.

*Anther diameter.*—0.1 cm.

*Pollen quantity.*—Moderate (normal quantity).

*Pollen color.*—RHS 12A.

*Female flowers.*—Not yet observed.

*Fertility/seed set.*—Has not been observed on this plant.

Disease/pest resistance: Disease/pest resistance has not been observed on this plant.

What is claimed is:

1. A new and distinct variety of *Poinsettia* plant named 'EURZ0027', substantially as illustrated and described herein.

* * * * *